(12) United States Patent
Beier et al.

(10) Patent No.: US 10,054,521 B2
(45) Date of Patent: Aug. 21, 2018

(54) BIOLOGICAL CELL AND TISSUE FIXATION BY LASER IRRADIATION

(71) Applicant: The United States of America as Represented by the Secretary of the Air Force, Washington, DC (US)

(72) Inventors: Hope T Beier, San Antonio, TX (US); Bennett Ibey, San Antonio, TX (US); Caleb C. Roth, San Antonio, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 73 days.

(21) Appl. No.: 14/670,067

(22) Filed: Mar. 26, 2015

(65) Prior Publication Data

US 2016/0282237 A1 Sep. 29, 2016

(51) Int. Cl.
*G01N 1/30* (2006.01)
*A01N 1/00* (2006.01)

(52) U.S. Cl.
CPC ............... *G01N 1/30* (2013.01); *A01N 1/00* (2013.01)

(58) Field of Classification Search
CPC ............... G01N 1/30; G01N 1/28; G01N 1/00
USPC .......................................................... 436/164
See application file for complete search history.

(56) References Cited

U.S. PATENT DOCUMENTS

| | | | |
|---|---|---|---|
| 4,891,239 A | 1/1990 | Dudley et al. | |
| 5,023,187 A | 6/1991 | Koebler et al. | |
| 7,687,255 B2 | 3/2010 | Chu | |
| 8,460,859 B2 | 6/2013 | Espina et al. | |
| 2010/0190177 A1* | 7/2010 | Emmert-Buck | G01N 33/543 435/6.14 |

FOREIGN PATENT DOCUMENTS

| | | |
|---|---|---|
| EP | 0241025 | 10/1987 |
| EP | 2126542 | 12/2009 |
| WO | 2008073187 | 6/2008 |
| WO | 2011071727 | 6/2011 |

\* cited by examiner

*Primary Examiner* — Christine T Mui
(74) *Attorney, Agent, or Firm* — AFMCLO/JAZ; Chastity Whitaker

(57) ABSTRACT

Systems and methods of fixing biological cells by laser irradiation. A method according to one embodiment of the present invention includes positioning a sample (of the cell or tissue) in a light pathway of a fixation source. The fixation source configured to emit electromagnetic radiation having a wavelength along the light pathway. The sample is exposed to the electromagnetic radiation for an exposure time.

19 Claims, 3 Drawing Sheets

BIOLOGICAL CELL AND TISSUE FIXATION BY LASER IRRADIATION

RIGHTS OF THE GOVERNMENT

The invention described herein may be manufactured and used by or for the Government of the United States for all governmental purposes without the payment of any royalty.

FIELD OF THE INVENTION

This invention relates generally to the field of fixation and preservation of biological specimens. More particularly, it relates to methods and systems for fixing and preserving a biological specimen using optical irradiation.

BACKGROUND OF THE INVENTION

The purpose of fixing biological specimens is to preserve the sample as close to its natural state as possible so that it may be examined later. Conventional fixation methods typically use physical means such as heat or freeze-drying, or chemical means, such as aldehydes (e.g., formaldehyde, paraformaldehyde, or glutaraldehyde) or alcohols (e.g., ethanol or methanol) to preserve a biological specimen for further preparation and examination. In heat fixation, a slide with a biological specimen is passed through a flame to adhere the specimen to the slide. Other methods of heat fixation include exposing the sample to microwaves (with or without the presence of chemical fixatives in the specimen). Samples may also be fixed with cold temperatures by freeze drying. In chemical fixation, the sample is immersed in the fixative that penetrates the specimen to preserve the sample. Many chemical fixatives, such as aldehydes, act to crosslink the proteins in the cells or tissues. Precipitating fixatives, such as alcohols, cause the proteins in the sample to precipitate or aggregate by reducing the solubility of the proteins or disrupting their tertiary structure.

These conventional methods suffer from a variety of limitations. Importantly, fixation using one or more of these current methods may disrupt the structure and composition of the cellular components, creating fixed samples that do not truly reflect the properties of the living cells or tissues. Conventional fixation methods often take several hours, meaning that the sample structure and/or properties may be altered while the fixation is occurring. Fixation may distort or alter the sample due to, for example, shrinkage upon dehydration of the sample or swelling/shrinkage upon placement of the specimen in a non-aqueous chemical fixative. Some components of the specimen (e.g., lipids) may also be lost during the fixation process. In addition, the conventional methods typically require that the entire sample contained in the sample container (e.g., slide, dish, etc.) be fixed at once. Furthermore, almost all fixation chemicals are extremely hazardous and special precautions must be taken to avoid accidental and/or chronic overexposure. The hazards associated with these chemicals range from inhalation and skin/eye contact hazards to severe flammability.

SUMMARY OF THE INVENTION

The present invention overcomes the foregoing problems and other shortcomings, drawbacks, and challenges of conventional fixation processes. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a method of fixing a sample includes positioning a sample in a light pathway of a fixation source. The fixation source configured to emit electromagnetic radiation having a wavelength along the light pathway. The sample is exposed to the electromagnetic radiation for an exposure time.

In accordance with another embodiment of the present invention, a method of fixing a sample includes positioning a sample in a light pathway of a fixation source. The fixation source configured to emit electromagnetic radiation having a wavelength along the light pathway. A first portion of the sample is exposed to the electromagnetic radiation for a first exposure time, and a second portion of the sample is exposed to the electromagnetic radiation for a second exposure time.

Yet another embodiment of the present invention includes a system for fixation of a biological sample. The system comprises a microscope, a fixation source, and beam delivery-focusing optics. The microscope is configured to visualize at least a portion of the biological sample. The fixation source is configured to emit an electromagnetic radiation having a wavelength and operably coupled to the microscope so as to irradiate the portion of the biological sample. And the beam delivery-focusing optics, which is positioned between the fixation source and the sample, is configured to adjust at least one parameter of the electromagnetic radiation.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
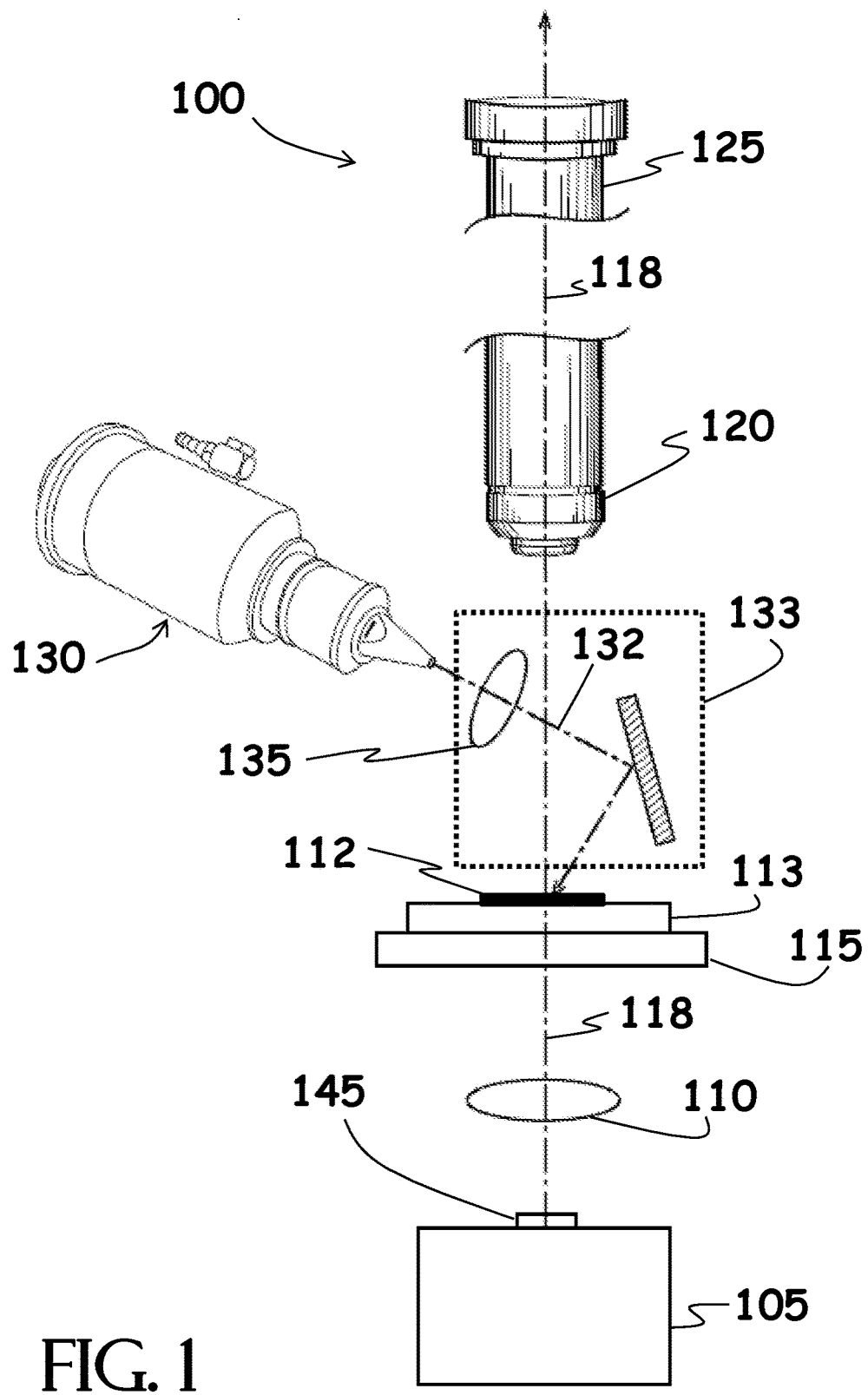
FIG. 1 is a side view of a first exemplary system according to the present invention comprising an optical microscope.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The present invention includes methods and systems for the histological fixation and preservation of biological specimens (cells or tissues) by acute exposure to electromagnetic radiation, including visible, ultraviolet, and infrared radiation. In some embodiments, the electromagnetic radiation comprises wavelengths ranging from about 100 nm to about 7,000 nm. Exposure of the biological specimen to a controlled dosage of electromagnetic irradiation preserves the material in its existing state so that it may be prepared for further examination at a later time. The presently disclosed methods and systems may be used to preserve samples for observation by techniques, such as optical techniques, tunneling electron microscopy (TEM), scanning electron microscopy (SEM), and atomic force microscopy (AFM), as well as to stabilize specimens for transportation. Biological fixation according to the present invention allows for a single region of interest of adjustable size to be fixed, while leaving the remainder of the cell culture or tissue viable for further examination and experimentation. This ability to achieve very controlled and limited fixation allows for multi-time point studies, potentially within in the same sample or specimen.

In addition, methods and systems according to the present invention achieve rapid fixation to reduce or eliminate many of the physiological or chemical changes in the sample that are commonly observed with other fixation processes due in part to the duration of the procedure. Because embodiments of the present invention achieves fixation in seconds to minutes—as opposed to hours or even days with conventional methods—a snapshot of a continuously changing microenvironment may be captured to provide optically fixed samples that may then be observed for morphological and chemical characteristics, as well as time-dependent changes within the same sample. The presently disclosed methods of fixation may also increase the mechanical stability or strength of the sample material to maintain the morphology of the sample. Proper fixation is particularly important for immunohistochemical or immunofluorescence methods that visualize molecular markers in cells using antibodies. Because of the size of the antibodies, use of these approaches with living cells is usually extremely difficult; as such, these methods typically employ fixed cells that have been made permeable. The presently disclosed methods and systems provide fixation procedures that may help to retain a level of reactivity to the antibodies and nucleic acid probes that more closely mimics living cells.

Referring to the drawings, wherein like reference numerals may designate like or corresponding parts throughout the several views, FIG. 1 is a side view of an exemplary system according to one embodiment of the present invention. The illustrated embodiment includes an optical microscope 100, wherein some components of the optical microscope 100 are omitted for clarity and to better illustrate certain aspects of the invention. The optical microscope 100 comprises a light source 105 and at least one condenser lens 110. The light source 105 is configured to generate light which illuminates a biological sample 112 on or in a sample container (illustrated here as a glass slide 113) on a sample stage 115. Examples of suitable systems may include, for example, an inverted or upright microscope, an inspection microscope, a telescope, or any other suitable combination of a lens system, either through an optical fiber or directly from the laser.

The biological sample 112 may be any cellular and tissue specimen obtained from in vivo and in vitro experiments and may include, for example, cells obtained by cell culture methods, a cell smear, cells isolated from a tissue section, or a tissue section. Cellular specimens may be stained, labeled, frozen, or otherwise treated and may be adherent or in suspension. The sample container 113 will vary based on the type of biological sample 112 and may comprise, for example, a microscope slide (such as the illustrated glass slide 113) with or without coverslip, a dish, a well plate, a petri dish, a cuvette, a capillary tube, a syringe, or any other suitable container configured to hold biological samples 112. The sample container 113 may comprise glass, plastic, or other suitable transparent material and may be a reflective or somewhat reflective to the electromagnetic radiation generated by the fixation source but also configured to transmit light from the light source 105. The sample container 113 may also be a substrate used for techniques such as AFM, TEM, and SEM. These substrates include, but are not limited to, mica, silicon, gold coated substrates, silicon nitride, crystals, quartz, and sapphire.

Referring again to FIG. 1, the light source 105 may include an electronic shutter 145 to control illumination of the biological sample 112 through the glass slide 113. The light emitted from the light source 105 (illustrated as beam 118 and defining a light pathway) and transmitted through the biological sample 112 on the glass slide 113 is transmitted to a microscope objective 120, which may contain one or more objective lenses and which is coupled to an eyepiece 125. The eyepiece 125 permits a user to observe a magnified view of the biological sample 112.

The optical microscope 100 according to the illustrated embodiment of FIG. 1 further comprises a fixation source 130 and a beam delivery-focusing optics (enclosed in dashed circle 133) comprising one or more lenses 135, one or more mirrors 140, or combinations thereof and is configured to deliver electromagnetic radiation from the fixation source 130 to the biological sample 112.

The fixation source 130 may comprise, for example, a laser, a light emitting diode, lamp, bulb, or other suitable source configured to produce one or more of visible light, ultraviolet light, or infrared irradiation (illustrated as beam 132 for the light pathway), and may be further configured to generate single wavelength, multiple wavelengths, continuous wave, quasi-continuous wave, or pulsed waves. In some embodiments of present invention, the fixation source 130 delivers visible, ultraviolet, and/or infrared radiation having wavelengths ranging from about 100 nm to about 7,000 nm. One of ordinary skill will understand that the components of the beam delivery-focusing optics 133 will be specific to each setup and may comprise, other than the lenses 135 and mirrors 140, one or more of optical filters, beam splitters, beam combiners, mirrors, and fiber cables. An electronic optical shutter (not labeled) may be placed in the optical path of the fixation source 130 to control the duration or exposure of the irradiation on the biological sample 112.

In the embodiment depicted in FIG. 1, the fixation source 130 is positioned external to the microscope 100 and between the microscope objective 120 and the biological sample 112 on the glass slide 113; however, such arrangement is not limiting and may be located at any suitable position within or without the optical microscope 100. For example, although not specifically shown, the fixation source 130 may be positioned within the microscope 100 and between the eyepiece 125 and the microscope objective 120 such that the electromagnetic radiation passes through the microscope objective 120 prior to striking the sample. Thus, a size of the light spot generated by the laser may be fixed to a specific diameter or changed by varying objectives or lenses. According to still other embodiment, not specifically illustrated herein, the fixation source 130 may be positioned on a side of the eyepiece 125 that opposes the objective 120 and the size of the light spot may be altered by using a telescope or other such beam expansion between the fixation source 130 and the eyepiece 125 and prior to the microscope.

It will be readily apparent to one skilled in the art having the benefit of the disclosure herein that illustrated embodiment of FIG. 1 may be preferable in instances where observation and positioning of the biological sample 112 is needed prior to or during fixation.

Figure 2:
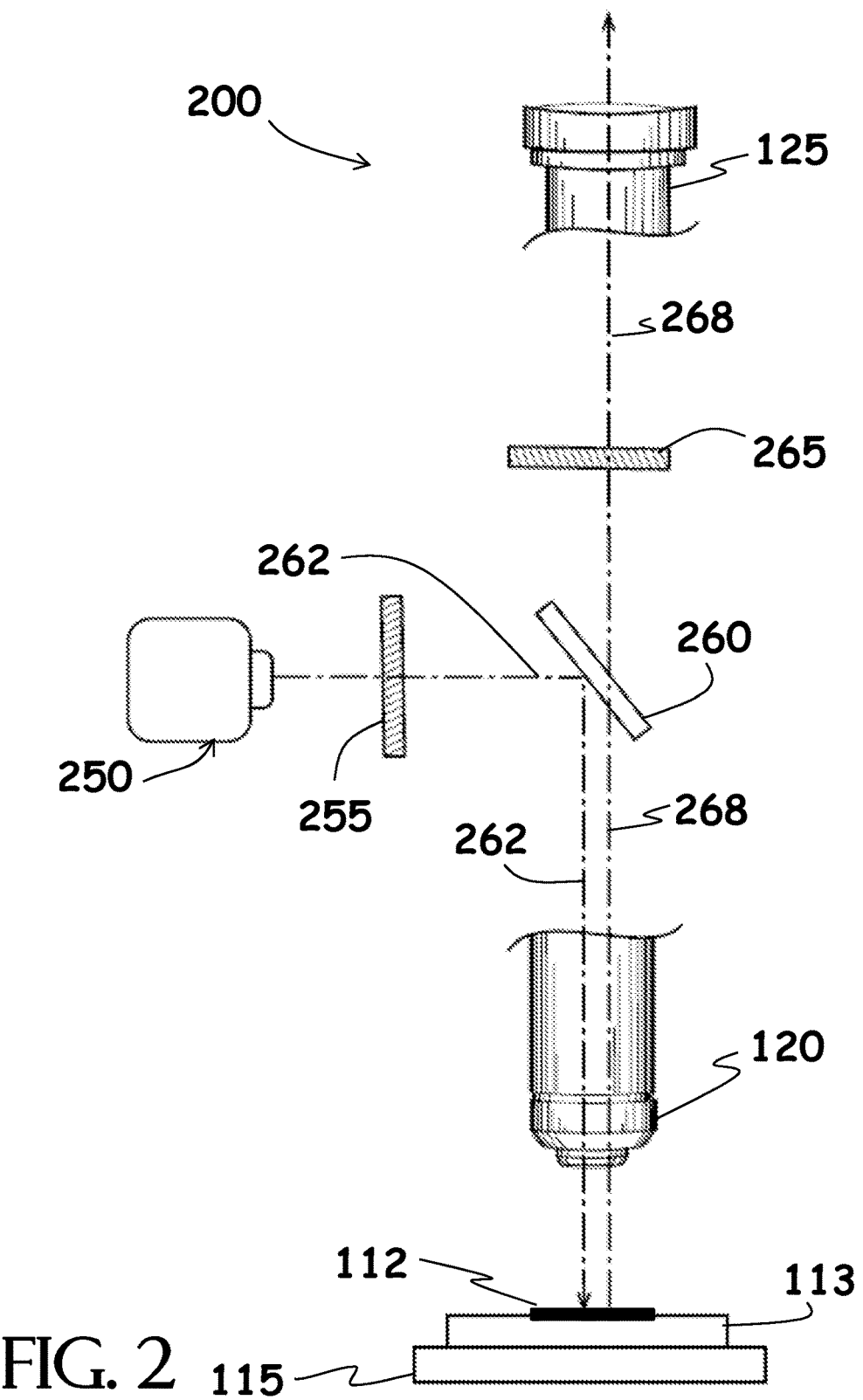
FIG. 2 is a side view of a second exemplary system according to the present invention comprising a fluorescence microscope.

Referring now to FIG. 2, wherein a side view of another exemplary system according to the present invention comprising a fluorescence microscope 200 is shown, a light housing 250 configured to contain both a light source and a fixation source (corresponding to the light source 105 and the fixation source 130, respectively, of FIG. 1) of within a single housing is shown. The light source may comprise, for example, a mercury or xenon lamp. Light (illustrated as beam 262), whether generated from the light source or the fixation source within the housing 250 is transmitted through one or more excitation filters 255. A beam splitter 260, which may comprise, for example, a dichroic mirror, reflects a portion of the light beam 262 transmitted through the filters 255 toward the microscope objective 120 onto a biological sample 112 on the glass slide 113. The light 262 may be absorbed by or reflected by or at the biological sample 112. In those instances when light 262 is absorbed by the biological sample 112 (or a dye or stain applied thereto), light of a different wavelength may be emitted (for example, fluorescent light) and is directed (illustrated as beam 268) away from the biological sample 112, through the beam splitter 260, to and through an emission filter 265, and, ultimately, toward the eyepiece 125 and user (not shown). Light reflected by the biological sample 112 or the glass slide 113 (or the stage 115) is also directed along the direction of beam 268.

It will be readily apparent to one skilled in the art having the benefit of the disclosure herein that illustrated embodiment of FIG. 2 may also be useful in instances where observation and positioning of the biological sample 112 is needed prior to or during fixation. However, one benefit to the illustrated embodiment of FIG. 2 is that the user (not shown) may optionally switch between operation of the light source, the fixation source, or both at the housing 250.

Figure 3:
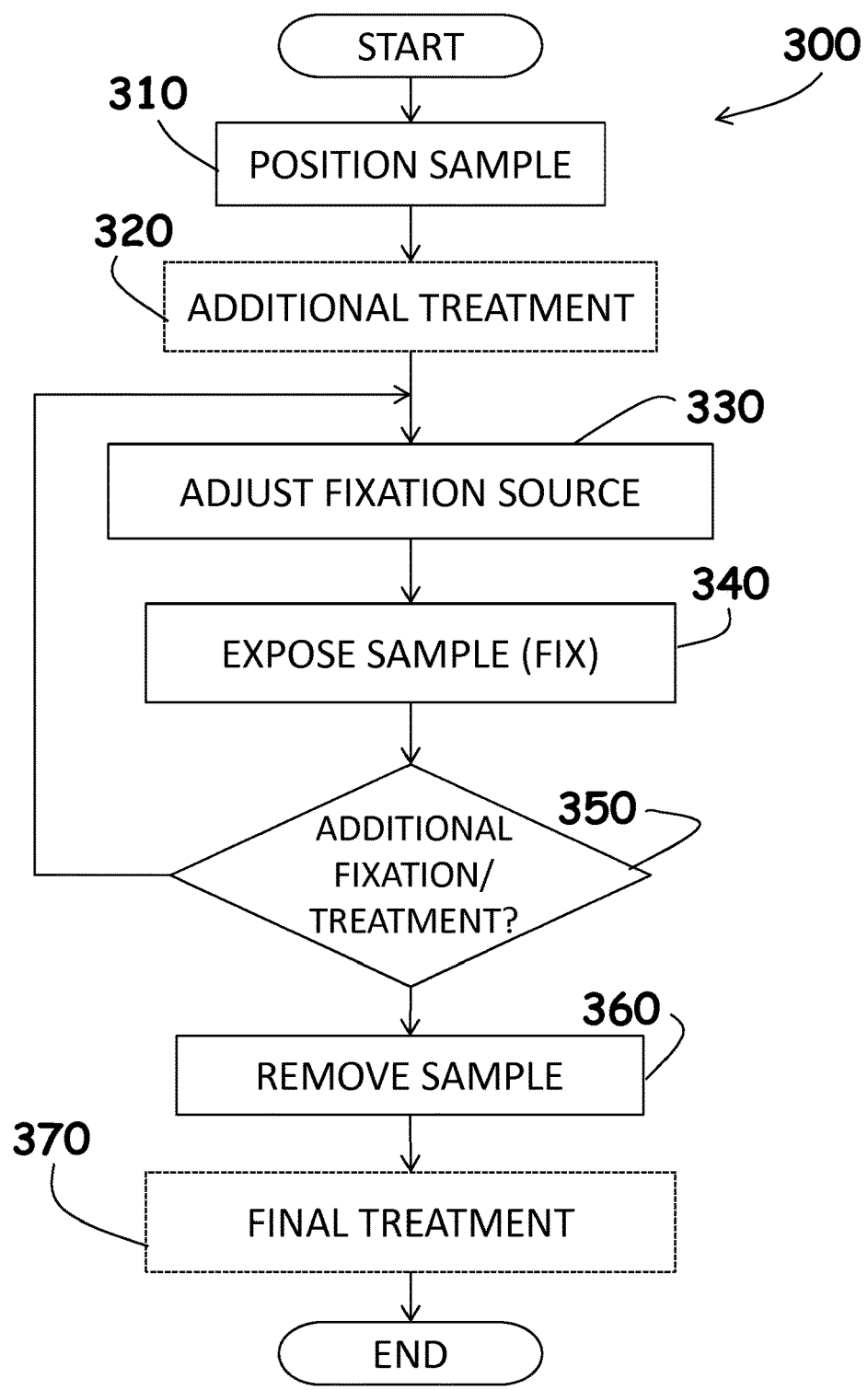
FIG. 3 is a flowchart illustrating a method of using the exemplary system of FIG. 1 in accordance with an embodiment of the present invention.

Turning now to FIG. 3 (with reference again to FIG. 1) a method of using embodiments of the present invention is shown. At start, the biological sample 112 is positioned with the glass slide 113 on the stage 115 such that a desired region or portion of the sample 112 to be fixed is located within a field of view or exposure area of the fixation source 130 (Block 310). Some embodiments of the method include, optionally, an additional treatment and/or manipulation of the biological sample 112, such as delivery of a pharmaceutical or probe or exposure of the sample to an experimental variable (Block 320). One or more parameters of the fixation source 130 and/or the beam delivery-focusing optics 133 may be adjusted (Block 330) as needed to achieve, for example, a desired wavelength, power, spot size, and/or distance between the fixation source 130 and the biological sample 112.

A portion of the biological sample is fixed 112 by exposing the biological sample 112 to electromagnetic radiation emitted from the fixation source 130. In that regard, the optical shutter (not shown) on the fixation source 130 is opened for a brief period of time (typically ranging from a few microseconds to a few minutes) in order to deliver a predetermined dosage of electromagnetic radiation having a specified wavelength to the biological sample 112. The dosage (generally measured in $J/cm^2$) may be calculated by multiplying the intensity or irradiance of the electromagnetic radiation (generally measured in $W/cm^2$) by the exposure time (generally measured in seconds or minutes).

Following fixation (Block 340), a determination is made whether additional fixation and/or treatment/manipulation of the biological sample 112 will occur (Decision Block 350). Where no additional handling of the biological sample 112 is desired ("No" branch of Decision Block 350), the biological sample 112 is removed (Block 360) and the method terminates. Where additional fixation and/or treatment/manipulation of the sample is desired ("Yes" branch of Decision Block 350), the method returns to further adjust one or more parameters of the fixation source 130 and/or the beam delivery-focusing optics 133 (Block 330) and continues until the desired number of iterations of additional fixation and/or treatment/manipulation of the biological sample 112 are achieved.

In some embodiments, the biological sample 112 and/or the sample container 113 may be repositioned one or more times to define a new field of view or exposure area. In other embodiments, additional treatment/manipulation of the biological sample 112 may be performed before additional fixation(s). In further embodiments, the repeated repositioning and/or treatment/manipulation of the biological sample 112 (in Block 320) and fixation (in Block 340) may be implemented as a routine into microscope software so that a "fixation" protocol may be selected to automate the fixation routine (such as using one or more stepper motors to manipulate the stage 105). With all treatments complete, the biological sample 112 is removed (step 360), and the method terminates.

In some embodiments, the biological sample 112 may still optionally undergo a final treatment (Block 370) to prepare the biological sample 112, for example, for additional post-fixation examination, transportation, and/or storage. This final treatment may include, for example, labeling with tagged antibodies specific to desired antigens or other labeling or staining techniques. By fixing multiple samples on a single slide, the presently disclosed method further allows for these different samples to be screened simultaneously with many different antibodies.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLE

Chinese hamster ovarian ("CHO-K1") cells were acquired from American Type Culture Collection (ATCC, Manassas, Va.) and cultured according to the supplier's protocol at 37° C. in 5% $CO_2$ and 95% humidity. F-12K Medium was supplemented with 10% FBS with 1 I.U./mL penicillin and 0.1 μg/mL streptomycin antibiotics. For experimentation, cells were grown on 35 mm glass-bottomcoverslip dishes that were demarcated into separate exposure areas. To prepare cells for labeling, cell media was removed by vacuum aspiration, the cells were rinsed twice with a buffered saline solution, and fresh buffer was added.

The cells were treated in accordance with embodiments of the present invention and using a fixation source consisting of a 488 nm argon laser positioned such that its beam is was routed through the epi-illumination pathway of an inverted microscope and through an objective lens. Prior to the microscope, the beam was expanded to fill an illumination diameter of about 150 µm at the sample plane. Laser exposures of 10 mW, 20 mW, and 50 mW were applied to the cells (about 50 $W/cm^2$, 100 $W/cm^2$, and 300 $W/cm^2$, respectively) for a test time period. After each exposure, the next area was selected and the cells were exposed to new test parameters.

To test whether the cells were fixed, the dishes were rinsed repeatedly with phosphate buffered saline solution to remove any non-fixed cells and then labeled with a fixed cell labeling kit to visualize the cellular structures. Exposures of 10 seconds, 30 seconds, 1 minute, 2 minutes, and 3 minutes at 10 mW or 20 mW all showed some level of cell fixation within the exposed areas. Exposures times of 2 minutes or longer showed consistent fixation at 10 mW. Exposures of 1 minute, 2 minutes, and 3 minutes with 50 mW all resulted in cell fixation (10 seconds and 30 seconds were not tested). Unexposed areas of the cell plate did not show any cells or fluorescence.

As provided herein, the present invention may be implemented as an integral part of a microscope of other suitable system or as an extension or modular add-on for an existing systems. The system may allow for light microscope observation of surrounding cells and tissue in a living state while simultaneously fixing cells at certain time points.

Because the methods and systems describe herein do not require the use of hazardous and/or flammable chemicals or the use of proper protective equipment (e.g., fume hoods, respirators, gloves, to name a few), it may also be used as part of a portable system to allow for fixation and/or inactivation in remote or flexible locations. In addition, fixation of samples using embodiments of the present invention may be performed by a layperson without formal training, reducing the number of specialists required at remote locations. The fixed samples and/or images of the fixed samples may then be sent to a central location for analysis or further preparation to detect or diagnose, for example, exposure to a biological agent. The ability to quickly preserve and safely maintain samples during transport is desirable to professionals in a variety of fields ranging from health professionals working in hazardous environments to research scientists collecting and preserving samples in the field. Safe and rapid preservation and inactivation of samples containing possible biological contaminants is particularly desirable to reduce the risk of outbreaks and increase the likelihood of proper diagnosis.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method for fixing a biological sample, the method comprising:
    positioning the biological sample on a surface of a substrate positioned in a light pathway of a fixation source, the fixation source configured to emit electromagnetic radiation having a wavelength along the light pathway;
    observing the biological sample;
    exposing a portion of the biological sample in the light pathway to the electromagnetic radiation for an exposure time such that the exposed portion of the biological sample is fixed; and
    observing a remaining portion of the biological sample.

2. The method of claim 1, wherein the beam delivery-focusing optics are positioned along the light pathway between the fixation source and the biological sample on the surface of the substrate, the beam delivery-focusing optics being configured to adjust at least one parameter of the electromagnetic radiation.

3. The method of claim 1, wherein the wavelength of the electromagnetic radiation ranges from 100 nm to 7,000 nm.

4. The method of claim 1, further comprising:
    adjusting a power level of the electromagnetic radiation, a spot size of the electromagnetic radiation, or both.

5. The method of claim 1, further comprising:
    pre-treating the biological sample before positioning the biological sample on the surface of the substrate and before positioning the biological sample and the substrate in the light pathway of the fixation source.

6. The method of claim 5, wherein pre-treating the biological sample includes applying one or more of a pharmaceutical, a probe, a stain, or a dye to the biological sample.

7. The method of claim 1, further comprising:
    chemically-treating the biological sample after the exposure time and after the biological sample is fixed to the surface of the substrate.

8. The method of claim 7, wherein chemically-treating includes applying one or more of an antibody, a label, a stain, and a dye to the biological sample.

9. The method of claim 1, further comprising:
    determining a dosage of the electromagnetic radiation applied to the biological sample; and
    optionally, continuing exposing the biological sample or terminating exposing the biological sample.

10. The method of claim 1, further comprising:
    supporting the biological sample with a sample container.

11. A method for fixing a biological sample to a substrate, the method comprising:
    positioning the biological sample on a surface of a substrate positioned in a light pathway of a fixation source, the fixation source configured to emit electromagnetic radiation having a wavelength along the light pathway;
    exposing a first portion of the biological sample in the light pathway to the electromagnetic radiation for a first exposure time such that the exposed first portion is fixed; and
    exposing a second portion of the biological sample in the light pathway to the electromagnetic radiation for a second exposure time such that the exposed second portion is fixed,
    wherein the first portion and the second portion represent first and second time points, respectively.

12. The method of claim 11, wherein the beam delivery-focusing optics are positioned along the light pathway and between the fixation source and the biological sample, the beam delivery-focusing optics being configured to adjust at least one parameter of the electromagnetic radiation.

13. The method of claim 11, further comprising:
adjusting a power level or a spot size of the electromagnetic radiation before exposing the second portion of the biological sample.

14. The method of claim 11, further comprising:
pre-treating the biological sample before positioning the sample in the light pathway of the fixation source.

15. The method of claim 14, wherein pre-treating the biological sample includes applying one or more of a pharmaceutical, a probe, a stain, or a dye to the biological sample.

16. The method of claim 11, further comprising:
chemically-treating the biological sample after the first exposure time.

17. The method of claim 16, wherein chemically-treating includes applying one or more of an antibody, a label, a stain, and a dye to the biological sample.

18. The method of claim 11, further comprising:
supporting the biological sample with a sample container.

19. A method for fixing a biological sample, the method comprising:
positioning the biological sample on a surface of a substrate positioned in a light pathway of a fixation source, the fixation source configured to emit electromagnetic radiation having a wavelength along the light pathway;
applying a pharmaceutical or a probe to the biological sample, the pharmaceutical or the probe configured to affect an observable feature of the biological sample;
exposing a first portion of the biological sample in the light pathway to the electromagnetic radiation for a first exposure time such that the exposed first portion is fixed;
after a period of time, exposing a second portion of the biological sample in the light pathway to the electromagnetic radiation for a second exposure time such that the exposed second portion is fixed; and
comparing the observable feature of first portion to the second portion.

* * * * *